United States Patent
Champagne

(10) Patent No.: US 12,236,586 B2
(45) Date of Patent: Feb. 25, 2025

(54) SYSTEM AND METHOD FOR CLASSIFYING DERMATOLOGICAL IMAGES USING MACHINE LEARNING

(71) Applicant: 2692873 Ontario Inc., Toronto (CA)

(72) Inventor: Trevor Champagne, North York (CA)

(73) Assignee: 2692873 Ontario Inc., Kamloops (CA)

( * ) Notice: Subject to any disclaimer, the term of this patent is extended or adjusted under 35 U.S.C. 154(b) by 394 days.

(21) Appl. No.: 17/587,688

(22) Filed: Jan. 28, 2022

(65) Prior Publication Data
US 2022/0245800 A1    Aug. 4, 2022

Related U.S. Application Data

(60) Provisional application No. 63/144,233, filed on Feb. 1, 2021.

(51) Int. Cl.
G06T 7/00 (2017.01)
G06F 3/01 (2006.01)
(Continued)

(52) U.S. Cl.
CPC .......... *G06T 7/0012* (2013.01); *G06F 3/013* (2013.01); *G06N 20/00* (2019.01); *G06T 3/40* (2013.01);
(Continued)

(58) Field of Classification Search
CPC .......... G06T 7/0012; G06T 3/40; G06T 7/11; G06T 2207/10016; G06T 2207/20021;
(Continued)

(56) References Cited

U.S. PATENT DOCUMENTS

2019/0139642 A1   5/2019  Roberge et al.
2019/0332931 A1  10/2019  Montantes
(Continued)

FOREIGN PATENT DOCUMENTS

CN    109191457 A  *  1/2019  .......... G06T 7/0012

OTHER PUBLICATIONS

Ronneberger, "U-Net: Convolutional Networks for Biomedical Image Segmentation", 2015. (Year: 2015).*

(Continued)

*Primary Examiner* — Juan A Torres
(74) *Attorney, Agent, or Firm* — Smart & Biggar LP

(57) ABSTRACT

Systems and methods using machine learning for classifying images as being sufficient for medical diagnosis. An example of the method includes: receiving a dataset comprising a plurality of medical images; receiving, from a first single source, a respective label for each one of the plurality of medical images, the respective label being a positive response versus a negative response; dividing each one of the plurality of medical images into a plurality of medical image segments; associating each one of the plurality of medical image segments with an image segment label based on the respective label for the respective medical image being divided; and training a machine learning model using: the plurality of medical images, the respective label for each one of the plurality of medical images, the plurality of medical image segments, and the respective image segment label of each one of the plurality of medical image segments.

20 Claims, 11 Drawing Sheets

(51) Int. Cl.
*G06N 20/00* (2019.01)
*G06T 3/40* (2006.01)
*G06T 7/11* (2017.01)
*G16H 30/20* (2018.01)

(52) U.S. Cl.
CPC .............. *G06T 7/11* (2017.01); *G16H 30/20* (2018.01); *G06T 2207/10016* (2013.01); *G06T 2207/20021* (2013.01); *G06T 2207/20081* (2013.01); *G06T 2207/20084* (2013.01); *G06T 2207/30088* (2013.01); *G06T 2207/30168* (2013.01)

(58) Field of Classification Search
CPC ........... G06T 2207/20081; G06T 2207/20084; G06T 2207/30088; G06T 2207/30168; G06F 3/013; G06N 20/00; G06N 3/045; G06N 20/10; G16H 30/20; G06V 10/774
USPC ......................................................... 382/128
See application file for complete search history.

(56) References Cited

U.S. PATENT DOCUMENTS

2020/0151873 A1* 5/2020 Armaitis ............... G06T 7/0012
2020/0184274 A1* 6/2020 Lee ........................ G06T 7/10
2020/0294234 A1 9/2020 Rance et al.
2020/0401843 A1 12/2020 Peng

OTHER PUBLICATIONS

Wang, "Segmentation of Multiple Structures in Chest Radiographs Using Multi-task Fully Convolutional Networks" 2017 (Year: 2017 ).*
Kaur, "Deep CNN-Based Method for Segmenting Lung Fields in Digital Chest Radiographs." 2017 (Year: 2017).*
Dai, "SCAN: Structure Correcting Adversarial Network for Organ Segmentation in Chest X-rays", 2017 (Year: 2017).*
Liu,. "SSD: Single Shot MultiBox Detector" 2016. (Year: 2016).*
Ren, "Faster R-CNN: Towards Real-Time Object Detection with Region Proposal Networks" 2016 (Year: 2016).*
Amendments received before examination EP4036867 dated Apr. 6, 2023 (Year: 2023).*
Amended claims filed after receipt of (European) search report EP4036867 dated Apr. 6, 2023 (Year: 2023).*
GB 2606255 A search report dated Jul. 27, 2022 (Year: 2022).*
Amendments received before examination EP4036867 dated Apr. 6, 2023 4 pages (Year: 2023).*
Gandomkar Ziba et al: "Predicting radiologists' true and false positive decisions in reading mammograms by using gaze parameters and image-based features", Progress in Biomedical Optics and Imaging, SPIE—International Society for Optical Engineering, Bellingham, WA, US, vol. 9787, Mar. 24, 2016 (Mar. 24, 2016), pp. 978715-978715.

* cited by examiner

FIG. 11

SYSTEM AND METHOD FOR CLASSIFYING DERMATOLOGICAL IMAGES USING MACHINE LEARNING

CROSS-REFERENCE

This application claims the benefit of priority to U.S. Provisional Patent Application No. 63/144,233 filed Feb. 1, 2021 entitled SYSTEM AND METHOD FOR CLASSIFYING DERMATOLOGICAL IMAGES USING MACHINE LEARNING, the entire contents of which are incorporated by reference into the Detailed Description herein below.

TECHNICAL FIELD

Example embodiments generally relate to the field of classifying medical images, such as dermatological images.

BACKGROUND

When used for diagnosis of lesions and skin conditions, machine learning models tend to be trained using a dataset (e.g. tumor images) that has been labelled with ground truth, such as a dataset including medical images labelled as "malignant" or "benign". Generally speaking, a machine learning model can be trained using to a set of labelled data, where the labels of the set of data indicate some knowledge about these data, then the machine learning model system can learn from the labelled data and apply, once the machine learning model is trained properly, what the machine learning model has learned to make a prediction when given a new set of unlabelled image data.

Images used to make a diagnosis or decide on a treatment are used extensively in dermatology and teledermatology. Sufficiently high image quality is required for a clinician or expert make a diagnosis, but there is little standardization in the literature or validated scales. Again, training a model to perform a full diagnosis can lead to high complexity without the confidence of a proper diagnosis by a clinician. As well, transmitting an uncompressed image to the clinician is wasted bandwidth and resources if that image is not suitable for the clinician to make a diagnosis.

SUMMARY

An example way to classify whether a medical image is good for diagnosis, is the individual opinion of a medical professional such as a clinician or a dermatologist: is the given image a "good quality" (i.e., good enough to make a diagnose) or "bad quality" (i.e., not good enough to make a diagnose)? A consultation request should have at least one good quality image for the purpose of determining the morphology of a skin eruption. Clinical image quality has also emerged as a concern for the longevity and cost-effectiveness of teledermatology. If the medical image is of insufficient quality, then clinician time is wasted in reviewing a bad quality image. Another image would then need to be retaken to replace the bad quality image with a good quality image, so that the good quality image can be further reviewed by the clinician. As well, bandwidth is wasted in transmitting the bad quality image to the clinician for review, even more so when the image is uncompressed.

An example embodiment is a method for training a machine learning model to classify a medical image. The method includes: receiving a dataset comprising a plurality of medical images; receiving, from a first single source, a respective label for each one of the plurality of medical images, the respective label being a positive response versus a negative response; dividing each one of the plurality of medical images into a plurality of medical image segments; associating each one of the plurality of medical image segments with an image segment label based on the respective label for the respective medical image being divided; and training a machine learning model for the first single source using: each one of the plurality of medical images, the respective label for each one of the plurality of medical images, each one of the plurality of medical image segments, and the respective image segment label of each one of the plurality of medical image segments.

In some embodiments, the method may further include: receiving a gaze profile for each one of the plurality of medical images from the first single source; and for each medical image of the plurality of medical image segments from the plurality of medical images, when the respective image segment label is a positive response: generating a gaze label for each one of the plurality of medical image segments for the medical image based on the received gaze profile for the medical image, and associating each one of the plurality of medical image segments with the respective gaze label; wherein the training of the machine learning model further comprises training the machine learning model for the first single source using: each one of the plurality of medical images, the respective label for each one of the plurality of medical images, each one of the plurality of medical image segments, the respective image segment label of each one of the plurality of medical image segments, and the respective gaze label of each one of the plurality of medical image segments.

In some embodiments, the machine learning model is not trained to make any medical diagnosis on any of the plurality of medical images.

In some embodiments, the gaze profile is generated based on tracking eye movements of the first single source and comprises a distribution of gaze hits from the first single source for the respective medical image.

In some embodiments, the respective label for each one of the plurality of medical images comprises a binary value.

In some embodiments, the binary value represents the positive response versus the negative response.

In some embodiments, the respective image segment label for each one of the plurality of medical image segments comprises an image segment binary value that represents the positive response versus the negative response, wherein the image segment binary value is based on the binary value of the respective label for the medical image containing the medical image segment.

In some embodiments, each one of the plurality of medical image segments has a minimum dimension of 224 pixels by 224 pixels.

In some embodiments, each one of the plurality of medical image segments has a dimension of 256 pixels by 256 pixels.

In some embodiments, the method may further include, before receiving the respective label for each one of the plurality of medical images, re-sizing each one of the plurality of medical images to a minimum of 720 pixels on one side of the respective medical image.

In some embodiments, the re-sizing of each one of the plurality of medical images is to 1024 pixels on the one side of the respective medical image.

In some embodiments, the machine learning model comprises at least one of: a support vector machine (SVM), linear regression, or a convolutional neural network (CNN).

In some embodiments, the medical images include dermatological images.

In some embodiments, the method may further include: receiving, from a second single source, a respective second label for each one of the plurality of medical images, the respective second label being the positive response versus the negative response; associating each one of the plurality of medical image segments of each one of the plurality of medical images with a second image segment label based on the respective second label for the respective medical image being divided; and training the machine learning model using the respective second label for each of the plurality of medical images and the second image label for each of the plurality of medical image segments from the plurality of medical images.

In some embodiments, having the positive response as the respective label for the medical image is an indication that the medical image has a quality sufficient for medical diagnosis.

In some embodiments, the method may further include: receiving additional information regarding each one of the plurality of medical images from the first single source; and associating each one of the plurality of medical images with the respective additional information; wherein the training of the machine learning model further comprises training the machine learning model for the first single source using: each one of the plurality of medical images, the respective label for each one of the plurality of medical images, each one of the plurality of medical image segments, the respective image segment label of each one of the plurality of medical image segments, and the respective additional information of each one of the plurality of medical images.

In some embodiments, the additional information regarding each one of the plurality of medical images includes one or more of: a dosage information, a likely diagnosis, or a treatment recommendation.

In some embodiments, at least one of the plurality of medical images is captured from a camera.

Another example embodiment is a method of classifying images, the method includes: receiving an image; dividing the image into a plurality of image segments; and for each image segment in the plurality of image segments, classifying, using a first trained machine learning model, the image segment as a positive image segment versus a negative image segment; when a threshold amount of the plurality of image segments are classified as the positive image segment by the first trained machine learning model, classifying the image as a positive medical image by the first trained machine learning model; and classifying, using a classification model, the image as the positive image when the image is classified as the positive image by the first trained machine learning model.

In some embodiments, the method may further include: for each image segment in the plurality of image segments: classifying, using a second trained machine learning model, the image segment as the positive image segment versus the negative image segment, and when the threshold amount of the plurality of image segments are classified as the positive image segment by the second trained machine learning model, classifying the image as the positive medical image by the second trained machine learning model; wherein the classifying of the image as the positive medical image by the classification model is classified when the image is classified as the positive medical image by the first trained machine learning model and the second trained machine learning model.

In some embodiments, the method may further include: for each image segment in the plurality of image segments: using a third trained machine learning model to classify the image segment as the positive image segment versus the negative image segment, and when the threshold amount of the plurality of image segments are classified as the positive image segment by the third trained machine learning model, classifying the image as the positive medical image by the third trained machine learning model; wherein the classifying of the image as the positive medical image by the classification model is classified when the image is classified as the positive medical image by at least a threshold number among the first trained machine learning model, the second trained machine learning model and the third trained machine learning model.

In some embodiments, the method may further include: for each image segment in the plurality of image segments: using a plurality of trained machine learning models to classify the image segment as the positive image segment versus the negative image segment, and when the threshold amount of the plurality of image segments are classified as the positive image segment by the respective trained machine learning model, classifying the image as the positive medical image by the respective trained machine learning model; wherein the classifying of the image as the positive medical image by the classification model is classified when the image is classified as the positive medical image by at least a threshold number among the first trained machine learning model and the plurality of trained machine learning models.

In some embodiments, the method may further include: outputting the respective classifying of the image as the positive medical image versus a negative medical image of each respective trained machine learning model.

In some embodiments, the method may further include: for each image segment in the plurality of image segments: classifying, using a second trained machine learning model, the image segment as the positive image segment versus the negative image segment, and classifying, using the classification model, the image segment as the positive image segment when the image segment is classified as the positive medical image segment by the first trained machine learning model and the second trained machine learning model; wherein the classifying of the image by the classification model as the positive medical image is classified when the threshold amount of the plurality of image segments are classified as the positive image segment by the classification model.

In some embodiments, the method may further include: for each image segment in the plurality of image segments, classifying, using a plurality of trained machine learning models to classify the image segment as the positive image segment versus the negative image segment, and classifying, using the classification model, the image segment as the positive image segment when the image segment is classified as the positive medical image segment by at least a threshold number among the first trained machine learning model and the plurality of trained machine learning models; wherein the classifying of the image as the positive medical image by the classification model is classified when the threshold amount of the plurality of image segments are classified as the positive image segment by the classification model.

In some embodiments, the first trained machine learning model, the classification model, and the method do not make a medical diagnosis based on the image.

In some embodiments, the method may further include: receiving the image from a video conference software application (facility).

In some embodiments, the first trained machine learning model is trained using a single source who is an end user of the video conference software application.

In some embodiments, the image is uncompressed.

In some embodiments, the method may further include: when the image is classified as the positive medical image by the classification model: extracting additional information regarding the image.

In some embodiments, the additional information regarding the image includes one or more of: a dosage information, a likely diagnosis, or a treatment recommendation.

In some embodiments, the additional information regarding the image is inferred by the first trained machine learning model.

In some embodiments, classifying the image as the positive medical image by the classification model is an indication that the image has a quality sufficient for medical diagnosis.

In some embodiments, the image include a dermatological image.

In some embodiments, the threshold amount of the plurality of image segments is learned by the first trained machine learning model or set by a system administrator.

Another example embodiment is a method for training a machine learning model, the method comprising: receiving a dataset comprising a plurality of medical images; receiving, from a first single source, a respective label for each one of the plurality of medical images, the respective label being a positive response versus a negative response; and training a machine learning model for the first single source using: each one of the plurality of medical images and the respective label for each one of the plurality of medical images; wherein having the positive response as the respective label for the medical image is an indication that the medical image has a quality sufficient for medical diagnosis, without making the medical diagnosis.

Another example embodiment is a method of classifying images, comprising: receiving an image; classifying, using a first trained machine learning model, the image as a positive image versus a negative image; classifying, using a second trained machine learning model, the image as the positive image versus the negative image; and classifying, using a classification model, the image as the positive image when the image is classified as the positive image by the first trained machine learning model and the second trained machine learning model; wherein having the positive response as the respective label for the image is an indication that the image has a quality sufficient for medical diagnosis, without making the medical diagnosis.

Another example embodiment is a system including: a processing device; and a memory coupled to the processing device, the memory storing machine-executable instructions that, when executed by the processing device, cause the processing device to perform any one of the above described methods.

Another example embodiment is a non-transient computer readable medium containing program instructions for causing a processing device to perform a method, the instructions including instructions for performing any one of the above described methods.

Another example embodiment is a system for training a machine learning model, the system includes: a processing device; and a memory coupled to the processing device, the memory storing machine-executable instructions that, when executed by the processing device, cause the processing device to: receive a dataset comprising a plurality of medical images; receive, from a first single source, a respective label for each one of the plurality of medical images, the respective label being a positive response versus a negative response; divide each one of the plurality of medical images into a plurality of medical image segments; associate each one of the plurality of medical image segments with an image segment label based on the respective label for the respective medical image being divided; and train a machine learning model for the first single source using: each one of the plurality of medical images, the respective label for each one of the plurality of medical images, each one of the plurality of medical image segments, and the respective image segment label of each one of the plurality of medical image segments.

Another example embodiment is a non-transient computer readable medium containing program instructions for causing a processing device to perform a method of training a machine learning model, the instructions including: instructions for receiving a dataset comprising a plurality of medical images; instructions for receiving, from a first single source, a respective label for each one of the plurality of medical images, the respective label being a positive response versus a negative response; instructions for dividing each one of the plurality of medical images into a plurality of medical image segments; instructions for associating each one of the plurality of medical image segments with an image segment label based on the respective label for the respective medical image being divided; and instructions for training a machine learning model for the first single source using: each one of the plurality of medical images, the respective label for each one of the plurality of medical images, each one of the plurality of medical image segments, and the respective image segment label of each one of the plurality of medical image segments.

BRIEF DESCRIPTION OF THE FIGURES

The features and advantages of example embodiments will become apparent from the following detailed description, taken in combination with the appended drawings, in which:

FIG. 11 shows an example of segmentation into 15×15 pixel squares of an image on a display screen for gaze tracking.

Figure 1:
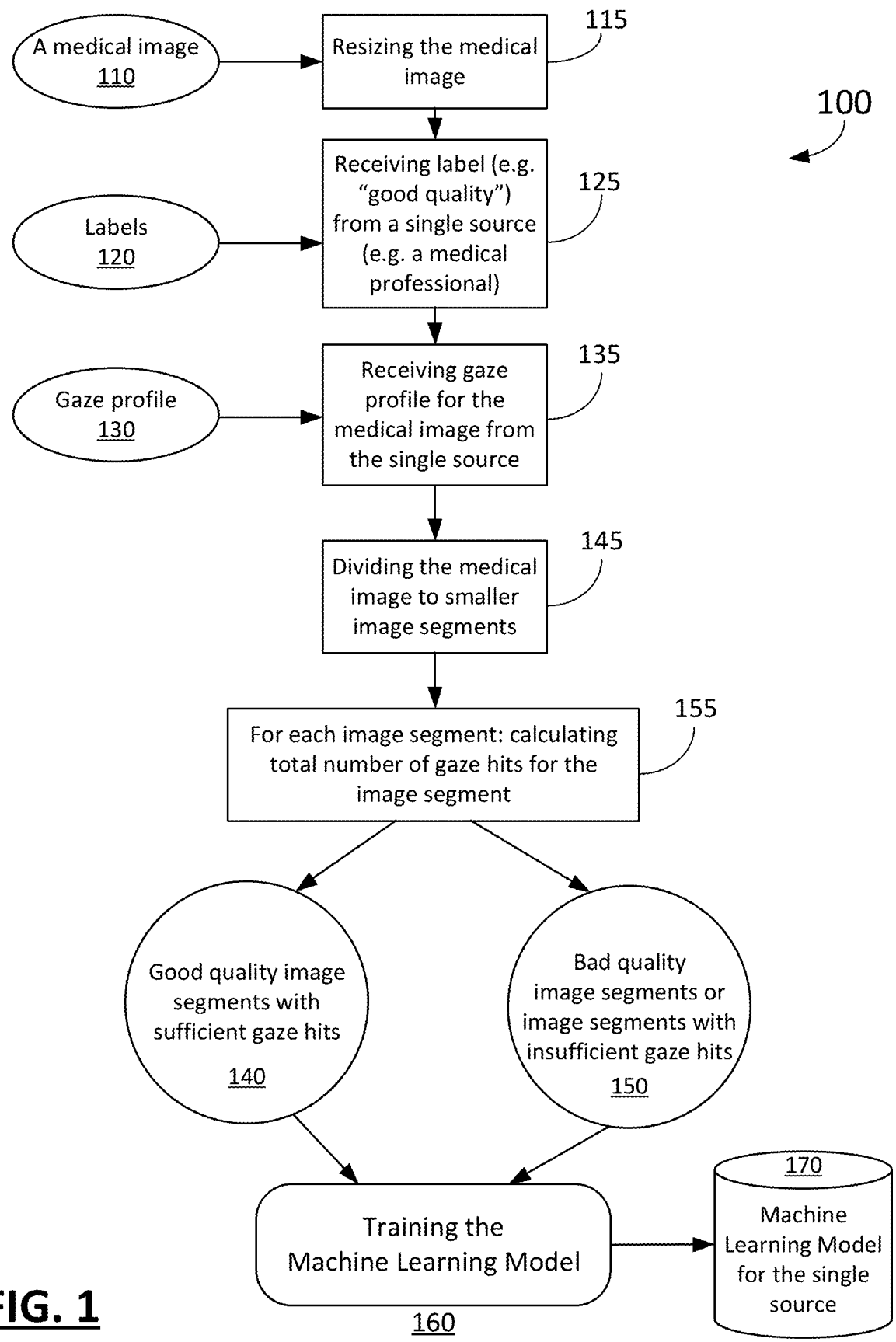
FIG. 1 shows a schematic diagram illustrating an example process of training a machine learning model to classify a medical image, in accordance with an example embodiment.

It is to be understood that throughout the appended drawings and corresponding descriptions, like features may be identified by like reference characters. Furthermore, it is also to be understood that the drawings and ensuing descriptions are intended for illustrative purposes only and that such drawings and descriptions are not intended to be limiting.

DETAILED DESCRIPTION

Various representative example embodiments will be described more fully hereinafter with reference to the accompanying drawings. Example embodiments may, however, be embodied in many different forms and should not be construed as limited to the representative embodiments set forth herein. In the drawings, the sizes and relative sizes of layers and regions may be exaggerated for clarity. Like numerals may refer to like elements throughout.

Example embodiments relate to systems and methods to train a machine learning model meant to surrogate the opinion of a single source, and, in some examples, their inclusion in yield management, performance, and clinical systems. The single source may a single expert, such as a medical professional, a clinician, and the like. The machine learning model, once properly trained, can receive a given image and generate a result classifying the given image as a "good quality" (positive) image or a "bad quality" (negative) image. Good quality, or a positive image, is an indication that the image has sufficient quality that makes it suitable for clinical use, such as making a medical diagnosis or clinical diagnosis. Bad quality, or a negative image, is an indication that the image does not have sufficient quality that makes it suitable for clinical use. Multiple machine learning models may be trained, where each respective machine learning model is trained based on opinions from a respective single source on the same set of medical images.

By using the opinions from one or more sources to train one or more machine learning models to identify images appropriate for medical or clinical uses, the technology provides an efficient system to quickly classify one or more images, which may be patient—uploaded image(s), or video frames from a live teleconference, as suitable or not suitable for a medical or clinical diagnosis. A user of the system, such a triage nurse or a doctor's assistant, may use the system to help guide the patient to upload or capture better quality images when appropriate, without necessarily involving a medical professional (e.g., a specialist doctor). The patient may also use the system, without help from any staff, to quickly ascertain if an image is suitable for a clinical or medical diagnosis. The patient can conveniently use the system while located remotely from the clinic or the clinician.

In some examples, note that the trained machine learning model from the single source does not need to make a classification or generate any outcome regarding an actual medical diagnosis based on a medical image, even though the machine learning model may be extensible to any opinion rendered by a dermatologist or other clinician, where the opinion may or may not represent a ground truth.

Example embodiments of the method differs from existing methods which attempt to obtain ground truth by pooling opinions from different sources into the labelling process of labelled dataset (e.g., three experts have agreed that an image shows a "dysplastic nevus" therefore the image is labelled as a "dysplastic nevus" for the purpose of training). Instead, in an example embodiment, the method keeps discordant labelling opinions and instead outputs that information separately: for example, Dr. A may label an image as "dysplastic nevus" and Dr. B may label the image as "normal nevus" but both labels are included in the training of a neural network, and disagreements can be acknowledged and resolved at the interpretation phase, where the results of Dr. A and Dr. B models are displayed, interpreted, and combined.

Some example embodiments can be implemented to simulate different clinical and nonclinical scenarios including triage by severity, choice of treatment, choice of consumer topicals, such as, for example, a choice of treatment likely prescribed by a single expert, a best location for someone to go to for management, and/or a most suitable clinician to go to for future management for a particular patient.

Some example embodiments can be implemented to simulate a single clinician having an opinion on a dataset of dermatoscopic and spectroscopic images (e.g. with dermatoscopes, contact dermatoscopes, optical coherence tomography, Spectrophotometric Intracutaneous Analysis (SIAscopy), and others). Some example embodiments can be implemented to simulate multiple clinicians having the same or different opinions on a dataset of dermatoscopic and spectroscopic images.

When an image or clinical photo (e.g. of an arm or a leg where there is significant background effect) is presented for a medical review or diagnosis, so long as a relevant portion of the image is good quality, the image may be rated as good quality for the purpose of medical review or diagnosis. In an example, the image is a dermatological image.

FIG. 1 shows a schematic diagram illustrating an example process 100 (training process or method) of training a machine learning model 170 to classify an image, such as a medical image 110 (which can be a dermatological image), in accordance with an example embodiment. In an example, the process 100 may be performed by the system 400 in FIG. 4, which is described in greater detail below. In the process 100, prior to step 115, the system 400 receives a medical image 110. At step 115, the system 400 resizes the medical image 110. In examples, the medical image 110 may be retrieved from a local or remote database. The medical image 110 may be resized to an appropriate or predefined size, such as to a minimum of 720 pixels along its shortest or longest side or axis. In some embodiments, the medical image 110 may be resized to have 1024 pixels on its shortest or longest side, which is intended to exceed the general recommendations in the literature that a diagnosable photograph has a longest axis of at least 720 pixels. Throughout the disclosure, for ease of discussion and illustration, an example of 1024 pixels may be used as the dimension of the resized medical image for classifying a medical image 110, it is to be appreciated that the medical image 110 may be resized to any other dimension as deemed appropriate by the system 400 or a system operator.

In some embodiments, a medical image 110 can be obtained from a dataset, such as a video, which includes a plurality of sequential images known a video frames, or time elapsed photos of the same area skin segment of the patient. For example, a medical image 110 can be a scan of a large region of the patient by way of video or time elapsed scan. The video frames or time elapse photos can then be presented to the single source one-by-one for training. In some embodiments, a medical image 110 may be a dermatological image.

At step 125, the opinion of a first single source, which may be a medical professional or a clinician 360, is received as a label 120 for the medical image 110, based on as whether or not he or she perceives it to be "good quality" or "not good quality". For instance, a "good quality" image may have a label 120 with a binary value of "1" and a "bad quality" image may have a label 120 with a binary value of "0". The software in some embodiments may present multiple medical images 110 to the medical professional or clinician 360 using a customized web interface, where the medical professional or clinician 360 may be prompted to selecting the "good quality" medical images in a rapid manner. For example, images 110 may be presented on a computer screen, one by one, and the medical professional or clinician 360 may press one input (key, button or voice) for "good quality" and another input (key, button or voice) for "not good quality" (or "bad quality"). For another example, images 110 may be presented on a computer screen, with multiple images displayed at once on one interface of a display device 350 (FIG. 3), and the medical professional or clinician 360 may select one or more from the multiple images as "good quality" images.

In some embodiments, in addition to, or in place of, labelling a medical image 110 dataset as "good quality" or "bad quality", the system 400 may also label the image 110 with other opinions from the medical professional or clinician 360, such as treatment plan, a dosage recommendation, a medical diagnosis, and so on.

At step 135, a gaze profile 130 for the image 110 may be received by the system 400. A gaze profile 130 may be obtained using a gaze tracking system installed at a computer system 380 (FIG. 3) used by the medical professional or clinician 360 who is viewing the image 110 on the display device 350.

Eye tracking refers to the process of measuring where the medical professional or clinician 360 look with their eyes, also known as a point of gaze. These measurements can be carried out by the gaze tracking system, that records the position of the eyes (where they are looking) and the movements they make. The gaze tracking system may be implemented using a number of technologies, such as, for example, a camera (e.g. a webcam or a mobile phone with camera capabilities), an infrared camera, and/or portable wearable technologies such as glasses or headset installed at the portal or computer used by the medical professional or clinician 360.

The image 110 is then marked (e.g. as a grid of pixel squares) and recorded using the gaze tracking system to determine one or more regions of diagnostic importance on the image 110. In general, the longer a medical professional or clinician 360 has concentrated his or her gaze within a particular area of the image 110, the more important that area of the image 110 may be when it comes to classifying the image 110. A mere glance can be defined as a gaze hit landing in an area of the image 110 for a very small amount of time (e.g., a fleeting moment such as 0.1 second) relative to the entire time (e.g. 5 seconds) the medical professional or clinician 360 spent looking at the image 110 as a whole. If an area or portion of the image 110 has only a very few glances from the medical professional, that area or portion may be considered insignificant in the process of classifying the image 110, and is disregarded by the gaze tracking system or the computer system 380.

For example, the gaze profile 130 for the image 110 can show a total number of gaze hits by the medical professional or clinician 360 within each 10×10 pixel square (or e.g. 15×15 pixel square, depending on the gaze tracking system used) in the image 110. The gaze profile may, in some embodiments, include distribution of gaze hits from the medical professional or clinician 360. For example, each 10×10 pixel square in the image 110 may be associated with a number of gaze hits, and the gaze profile may include multiple pairs of $[N_i, G_i]$ in a data array, where $N_i$ represents a respective image square, and G represents a number of gaze hits received by the respective image square from the medical professional or clinician 360, i=0 . . . n, where n is the total number of image squares in the image 110.

In some embodiments, a number of gaze hits G may also indicate a level of gaze duration in a given area of interest. For example, if the gaze tracking system captures the gaze of the medical professional or clinician 360 at a sampling rate of 30 Hz, when the medical professional or clinician 360 spends 3 seconds in a particular area of interest, such as the $N_i$ image square, the gaze tracking system may compute $G_i$=90 gaze hits in the $N_i$ image square during the 3 seconds for the $N_i$ image square. Therefore, for a given period of time, the longer the medical professional or clinician 360 concentrates his or her gaze in a particular area, the higher the total number of gaze hits will be in that particular area.

In some embodiments, the gaze profile may be represented using a heat map, which is a visualization of pupil-fixation positions over time. For example, when the medical professional or clinician 360 has concentrated his or her gaze in a particular area of interest in the image 110 for a first minimum number of gaze hits (e.g. 100 hits) or a first minimum of amount of time (e.g. 5 seconds), that area of interest may be assigned a heat level of 5 and assigned a colour of red for representation; when the medical professional or clinician 360 has concentrated his or her gaze in a particular area of interest in the image 110 for a second minimum number of gaze hits (e.g. 100 hits) or a second minimum of amount of time (e.g. 3 seconds) but below the first minimum number of gaze hits or the first minimum of amount of time, that corresponding area of interest may be assigned a heat level of 3 and assigned a colour of orange for representation; and when the medical professional or clinician 360 has concentrated his or her gaze in a particular area of interest in the image 110 for less than the second minimum number of gaze hits or the second minimum amount of time, that corresponding area of interest may be assigned a heat level of 1 and assigned a colour of blue or green for representation. An area of interest may be predefined to be a particular size, such as 100×100 pixel, or 200×300 pixel, and so on. The first or second minimum number of gaze hits or first or second minimum amount of time may be learned by the machine learning model in some examples, or predefined in other examples.

At step 145, the medical image 110 is then divided into multiple image segments. Each image segment may have a size consistent with a pixel resolution used by the applicable neural network in the machine learning model 170. For example, an image segment may have a size of 224 pixel× 224 pixel, 256 pixel by 256 pixel, or 299 pixel by 299 pixel. In some embodiments, the size of image segments may be set by a system administrator. An image segment label for each one of the plurality of medical image segments may be generated and contain an image segment binary value that represents a positive response versus a negative response, where the image segment binary value is based on the binary value of the respective label for the medical image 110 containing the medical image segment. For example, if the respective label for the medical image 110 has a binary value of "1" indicating a positive response or good quality, the corresponding image segment label for each of the image segments in the medical image 110 also has a binary value of "1" indicating a positive response or good quality. For another example, if the respective label for the medical image 110 has a binary value of "0" indicating a negative response or bad quality, the corresponding image segment label for each of the image segments in the medical image 110 also has a binary value of "0" indicating a negative response or bad quality.

In some embodiments, a gaze label (not shown in FIG. 1) may be generated for each image segment based on the gaze profile 130 for the image 110. For the purpose of the discussion, the image segment size is assumed to be, for example, 256 pixel×256 pixel, and it is to be appreciated that the image segments in the image 110 may have other sizes (e.g., 224×224 or 299×299). Each 256×256 image segment in the image 110 may contain a number of image squares (which may be 10×10, 20×20, or another size as defined by the system 400), where each image square has a corresponding number of gaze hits based on the gaze profile 130 for the image 110, and the gaze label for a particular 256×256 image segment may include a total number of gaze hits equivalent to the sum of all gaze hits captured by the 256×256 image segment. In some embodiments, if the gaze profile 130 is a heat map as described above, then the gaze label for a 256×256 image segment can simply be a smaller heat map taken from the gaze profile 130 for that particular 256×256 image segment.

Generally speaking, a gaze label for an image segment is a representation of how much interest the particular image segment has gathered from the medical professional or clinician 360 while he or she assessed the image 110 for its suitability or quality as an image that may be appropriate for medical or clinical diagnosis. Since a medical image 110 may have important area (e.g., skin lesion) and unimportant area (e.g., background), distinguishing image segments by area of interest based on tracking the eye movements of the medical professional or clinician 360 is an efficient method of labelling and training the machine learning model 170 to learn which image segment may contain salient features for medical or clinical diagnosis.

In some embodiments, in process 100, resizing and segmentation steps (e.g., steps 115, 135) can be omitted for dermatoscopic or spectrophotometric images.

At step 155, each image segment (or the image 110 if not divided into image segments) may be associated with a corresponding number gaze hits that landed within the segment based on a gaze label, which can be determined based on the gaze profile 130 for the medical image 110. When an image segment has sufficient number of gaze hits that is above a learned or set threshold (e.g., 20 gaze hits per 256×256 pixel), the image segment may be labelled by the system 400 as "having sufficient gaze hits" or "important"; otherwise, the image segment may be labelled by the system 400 as "having insufficient gaze hits" or "unimportant". The "important" segments, depending on the label of the image, are then individually labelled according to the quality ascertained for the entire image. In some embodiments, the gaze label may simply be "important" or "unimportant" based on the total number of gaze hits in the respective image segment.

Each image segment, now implicitly labelled with "important" or "not important", and also labelled as "good quality" or "bad quality", can be, in some embodiments, manually reviewed by the medical professional or clinician 360, and then used to train the machine learning model 170, such as a neural network. The neural network may be a random new network, or incorporate transfer learning from earlier iterations (for example, Dr. A trains the network, and Dr. B retrains the new network with fewer samples to be more specific for the needs of Dr. B).

In some embodiments, a plurality of medical images $M_i$ 110 may be received by the system 400 for training the machine learning model 170, i=1 . . . T, where T is the total number of the plurality of medical images. Each of the plurality of medical images $M_i$ 110 may be divided into a plurality of medical image segments. For each medical image $M_i$ 110 of the plurality of medical image segments, when the respective image segment label is a positive response, the method can include: generating a gaze label for each one of the plurality of medical image segments for the medical image $M_i$ based on the received gaze profile for the medical image $M_i$; and training the machine learning model 170 for the first single source using each one of the plurality of medical image segments from the plurality of medical images 110, where each one of the plurality of medical image segments is associated with a respective image segment label and a respective gaze label when the respective image segment label is positive.

In an example, the process 100 can be performed on multiple medical images 110 of a suitable sample size, and the process 100 is repeated (looped) in series to receive the next medical image 110 prior to step 115. In some embodiments, after multiple medical images 110 are received and processed by the system 400, image segments 140 with sufficient gaze hits (i.e., "important") and labelled as good quality are sent, as one set of labelled datasets, to machine learning training process 160 to train the machine learning model 170 (e.g., neural network). At the same time, image segments 150 with insufficient gaze hits (i.e., "unimportant"), and/or image segments 150 labelled as bad quality are sent, as another set of labelled datasets, to machine learning training process 160 to train the machine learning model 170 (e.g., neural network). In some embodiments, each one of the plurality of medical images 110, the respective label for each one of the plurality of medical images, each one of the plurality of medical image segments 140, the respective image segment label of each one of the plurality of medical image segments 140, and if applicable, the respective gaze label of each one of the plurality of medical image segments 140 may be sent to the machine learning training process 160 to train the machine learning model 170. In some embodiments, when the medical professional or clinician 360 has sent additional information (e.g. additional auxiliary information) to the system 400 regarding each medical image 110, such as a dosage information, a likely diagnosis, or a treatment recommendation, the additional auxiliary information may be also sent to the machine learning training process 160 to train the machine learning model 170 along with the plurality of medical images 110.

The trained machine learning model 170 can have the ability to differentiate between image segments that are good or bad quality (or, in the case of dermoscopy and other single-lesion imaging techniques, a single decision for the entire image). In some embodiments, a machine learning model 170 is not trained to make a medical diagnosis based on any of the plurality of medical images 110.

In some embodiments, the trained machine learning model 170 may be implemented using support vector machine (SVM), linear regression, or convolutional neural network (CNN). The input image 110 may be represented by a matrix. Each of the neural network layers of the trained machine learning model 170 can be represented by a matrix.

The CNN may include one or more convolution layers and one or more pooling layers. The convolution layer is configured to carry out convolution operation using a kernel or filter to process an input image. The kernel may be a matrix with a smaller dimensions than the matrix representing the image. The convolution layer is configured to extract features of the input image, such as edges, color, gradient orientation. The pooling layer is configured to extract dominant features that are rotational and positional invariant. The pooling layer thus further reduces the spatial size of the convoluted image features and reduce the dimensionality of the matrix to be processed. The pooling layer is configured to perform Max Pooling or Average Pooling. Max Pooling returns the maximum value from the portion of the image covered by the Kernel. Average Pooling returns the average of all the values from the portion of the image covered by the Kernel.

The CNN may include a fully-connected layer for learning non-linear combinations of the high-level features as represented by the output of the convolutional layer. The fully-connected layer receives the output of the convolution layer and/or the pooling layer and predicts the best label to describe the input image, such as the positive response versus the negative response. The fully-connected layer is configured to learn a possibly non-linear function in the space represented by the output of the convolutional layer.

In some embodiments, the process 100 may include further training the machine learning model 170 using input from one or more single sources that are different from the first single source. For example, the process 100 may include: receiving, from a second single source (e.g. a second medical professional or clinician 360), a respective second label for each one of the plurality of medical images 110, the respective second label being a positive response versus a negative response; associating each one of the plurality of medical image segments of each one of the plurality of medical images with a second image segment label based on the respective second label for the respective medical image being divided; and training the machine learning model 170 using each one of the plurality of medical image segments from the plurality of medical images. In some embodiments, the process 100 may include training the machine learning model 170 using a third single source (e.g. a third medical professional or clinician 360).

In some embodiments, when training the machine learning model 170 using input from a second or third medical professional or clinician 360, steps 115 to 160 are performed for each medical professional or clinician 360.

In some embodiments, each individual machine learning model 170 is trained based on the input from a respective single source. For example, referring a first machine learning model 170 is trained based on input from the first medical professional or clinician 360, a second machine learning model 170 is trained based on input from the second medical professional or clinician 360, a third machine learning model 170 is trained based on input from the third medical professional or clinician 360, and so on.

Figure 2:
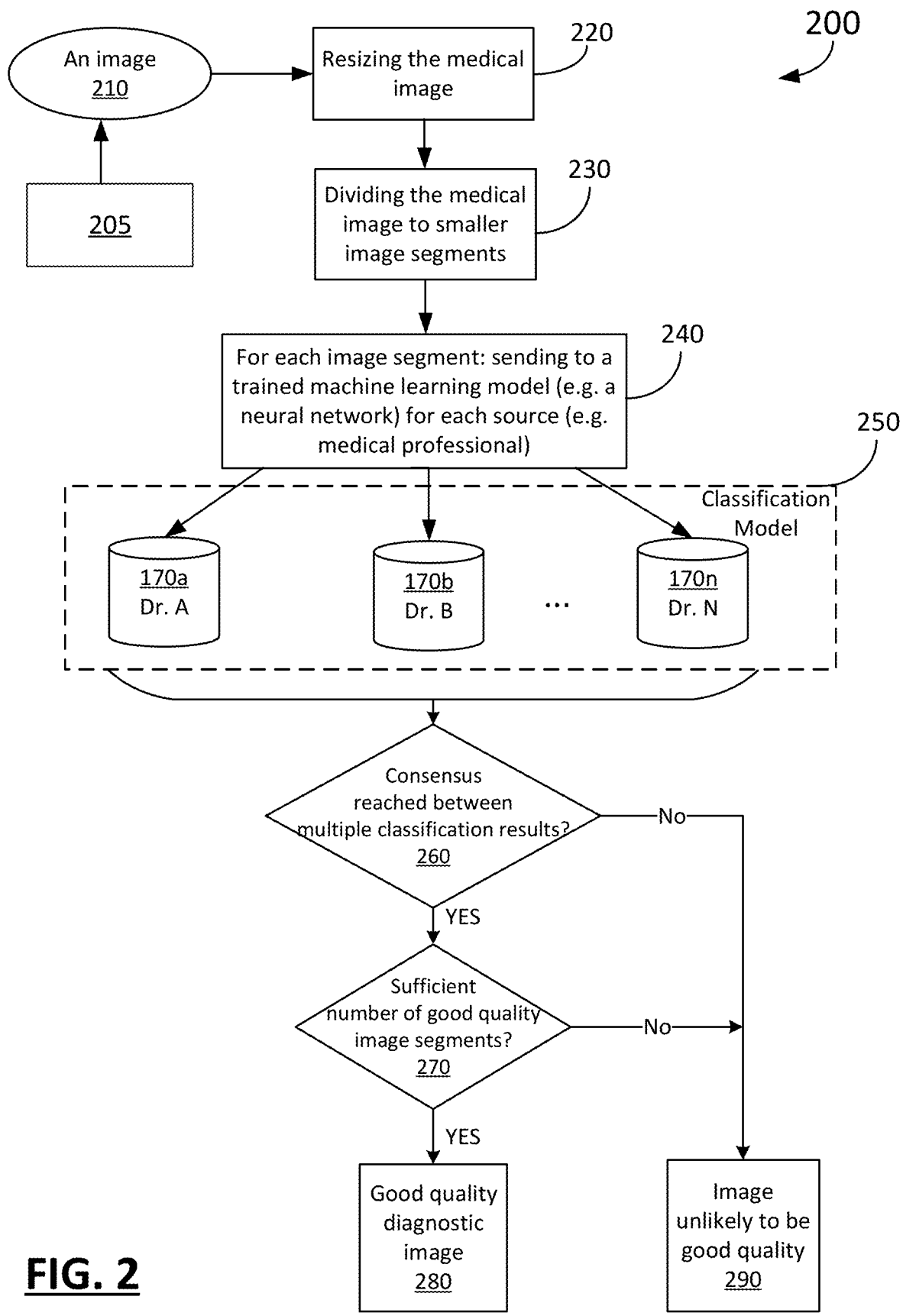
FIG. 2 shows a schematic diagram illustrating an example process of using one or more trained machine learning models to classify an image, in accordance with an example embodiment.

FIG. 2 shows a schematic diagram illustrating an example process 200 (inference process or method of classifying images) of using one or more trained machine learning models 170a, 170b . . . 170n to classify an image 210, in accordance with an example embodiment.

The training process 100 described in connection with FIG. 1 produces a number of machine learning models 170: in the present example, first machine learning model 170a (e.g., neural network) was trained using input from Dr. A, second machine learning model 170b (e.g., neural network) was trained using input from Dr. B, and nth machine learning model 170n (e.g., neural network) was trained using input from Dr. N. In an example embodiment, one or more machine learning models 170a, 170b . . . 170n may be used, depending on the needs of the system 400, the clinician 360, and the patient. When multiple machine learning models 170a, 170b, 170n are used, each machine learning model 170a, 170b . . . 170n may generate a single respective surrogate decision, on a single image or a single image segment, which may be a dermatoscopic or a clinical image.

Because of the flexibility of the training process 100, these respective machine learning models 170a, 170b, 170n are then grouped according to the needs of the eventual stakeholder. As further elaborated below in association with FIG. 2, in some embodiments, one or more stakeholder(s) may require a consensus among different machine learning models 170a, 170b . . . 170n to determine that a medical image qualifies as "good quality" or "bad quality". In some cases, a consensus may mean an unanimous decision. In other cases, a consensus may mean an agreement by a majority of the machine learning models 170a, 170b . . . 170n. The stakeholder may request machine learning models 170a, 170b . . . 170n to be separated by regional dermatologists. The stakeholder may want to see all results from all machine learning models 170a, 170b . . . 170n, for example, if a patient is directly soliciting multiple opinions through multiple models as to whether a lesion is dangerous or benign.

In an example embodiment of FIG. 2, the process 200 may include: receiving an image 210, dividing the image 210 into a plurality of image segments; and for each image segment in the plurality of image segments, using one or more trained machine learning models 170a, 170b . . . 170n to classify the image segment as a positive image segment ("positive") versus negative image segment ("negative"); and when a threshold amount of the plurality of image segments in the image 210 are classified as positive by at least one of the one or more trained machine learning model 170a, 170b . . . 170n, the classification model 250 classifies the image 210 as a positive medical image. The threshold amount of the plurality of image segments in the image 210 that need to be classified as positive before the image 210 is classified as a positive medical image may be predefined by a system administrator or a system user in some examples, or learned by the classification model 250 in other examples. In some embodiments, the threshold amount of the plurality of image segments in the image 210 that need to be classified as positive may be set dynamically or set based on context dependent on the rest of the plurality of image segments in the image 210. In an example, the threshold amount can be context-dependent on the quality of the image 210 being received.

In some examples, the process 200 determines a certain type of consensus reached between the various trained machine learning models 170a, 170b . . . 170n with respect to a single image segment before a final decision (e.g. a positive response versus a negative response) on the image segment can be classified by the classification model 250 of the system 400. For example, when a plurality of trained machine learning models 170a, 170b . . . 170n are used, a threshold number or portion of the plurality of trained machine learning models 170a, 170b . . . 170n need to determine that the image segment is a positive image segment before the classification model 250 of the system 400 may classify the image segment as positive. In some embodiments, when a plurality of trained machine learning models 170a, 170b . . . 170n are used, at least a majority (e.g. two out of three or three out of three) of the machine learning models 170a, 170b . . . 170n need to determine that the image segment is a positive (or negative) image segment before the classification model 250 of the system 400 may classify the image segment as a positive or negative image segment. When consensus is reached, the classification model 250 classifies the single image segment as positive.

In an example, all (i.e., unanimous) of the plurality of trained machine learning models 170a, 170b . . . 170n need to determine that the image 210 is a positive image before the classification model 250 classifies the image 210 as positive. In another example, at least a majority (e.g. two out of three) of the machine learning models 170a, 170b . . . 170n need to determine that the image 210 is a positive (or negative) image before the classification model 250 classifies the image 210 as a positive or negative image.

In some embodiments, the threshold number of trained machine learning models 170a, 170b . . . 170n required to reach consensus is learned by the classification model 250. In some examples, the threshold number can be context-dependent on the quality of the image 210 being received.

The implementation endpoints involved in process 200 may include: a system 205 or a web portal thereof for assessment of images; SaaS (Software as a service) for integration into one or more health portals; end-user application(s), for embedding in end-user videoconferencing software, as a method of identifying key frames and clear images that could be used for diagnosis, and sent independently to the dermatologist or clinician 360 without the compression that occurs with typical videoconferencing software, and/or hardware and software for using wearable AR (augmented reality), where the camera images from the wearable AR are sent to an integrated or remote server, then presented to the wearer (e.g. the patient) and/or the dermatologist or clinician 360.

Prior to step 220, the image 210 is received from the system 205 accessed by a user, such as from a web portal of the system 205 used by a patient. The image 210 may be, for example, a medical image 210. The image 210 may be, for example, an image shown in FIGS. 5 to 10 that is taken by the patient using a web camera, digital camera or a mobile phone. At step 220, the image 210 may be resized to an appropriate size, such as to 1024 pixels along its shortest or longest side or axis. Throughout the disclosure, for ease of discussion and illustration, an example of 1024 pixels may be used as the dimension of the resized medical image for classifying the image 210, and it is to be appreciated that the image 210 may be resized to any other dimension (e.g., 720 pixels along its shortest or longest side) as deemed appropriate by the classification model 250 of the system 400, the clinician 360, or a system administrator.

At step 230, the medical image 210 may be divided to smaller image segments, such as divided into multiple 256×256 image segments. In some embodiments, the medical image 210 may be divided into image segments of other sizes, such as 224×224, or 299×299 pixels.

In some embodiments, in process 200, resizing and segmentation steps (e.g., steps 220, 230) can be omitted for dermatoscopic or spectrophotometric images.

At step 240, for each image segment in the image 210, the image segment is sent to one or more trained machine learning models 170a, 170b . . . 170n for the classification model 250, where each of the one or more trained machine learning model 170a, 170b . . . 170n acts as a surrogate for a single source (e.g. a single medical professional or clinician 360) and the classification model 250 can generate a respective classification result for the image segment.

The classification model 250 may generate one or more classification results, depending on the number of trained machine learning models 170a, 170b . . . 170n, for each image segment in the image 210.

The system 400 may be implemented to, at step 260, when multiple trained machine learning models 170a, 170b . . . 170n have generated multiple classification results for the same image segment, achieve a consensus or agreement between the various classification results. For example, an image segment (or the image if not divided into segments) can have a minimum of N/2 "good quality" or positive classification results, where N is the total number of machine learning models 170a, 170b . . . 170n used, in order to be classified by the classification model 250 of the system 400 as a "good quality" or positive image segment.

In another example, for the system 400, the image segment (or the entire image if not divided into segments) may need to have "good quality" classification results from machine learning models 170a and 170b, in order to be classified by the classification model 250 of the system 400 as a good quality image segment.

In yet another example, the image segment (or the image if not divided into segments) may need to have a positive "good quality" classification result from all of the trained machine learning models 170a, 170b . . . 170n (i.e., a unanimous result), in order to be classified by the classification model 250 of the system 400 as a good quality image segment.

At step 260, the process 200 makes a decision as to if there are sufficient number of good quality image segments in the image 210 (e.g., at least 80%), before deciding if the image 210 is a good quality diagnostic image 280, or it may be an image 290 that is unlikely to possess sufficient quality for diagnostic purposes.

At step 270, the classification model 250 of the system 400 may, in some embodiments, further verify if there is a consensus or agreement between the multiple trained machine learning models used 170a, 170b . . . 170n. For example, each machine learning model 170a, 170b . . . 170n may classify the image 210 as "good quality" or "bad quality" first based on if there is a sufficient number of good quality image segments in the image 210, then in some examples, the classification model 250 of the system 400 may decide that there is an agreement between the various machine learning models 170a, 170b . . . 170n and the image 210 is therefore classified as a good quality diagnostic image 280, otherwise it may be an image 290 that is unlikely to possess sufficient quality for diagnostic purposes. An agreement between the various machine learning models 170a, 170b . . . 170n may be reached when at least a majority (e.g. 50% or higher) of the machine learning models 170a, 170b . . . 170n decide that the image 210 is a good quality diagnostic image 280. When agreement is reached, the classification model 250 classifies the image 210 is a good quality diagnostic image 280.

In some embodiments, the medical image 210 may be classified as a "good quality" image suitable for medical or clinical diagnosis, and marked suitable for a subsequent video conference, in which case the image 210 may be transmitted (e.g. via e-mail) to a medical professional or clinician 360 for review and/or diagnosis. If the image 210 is classified as a "bad quality", then the image 210 is not used for any subsequent video conference nor sent to any medical professional.

Figure 3:
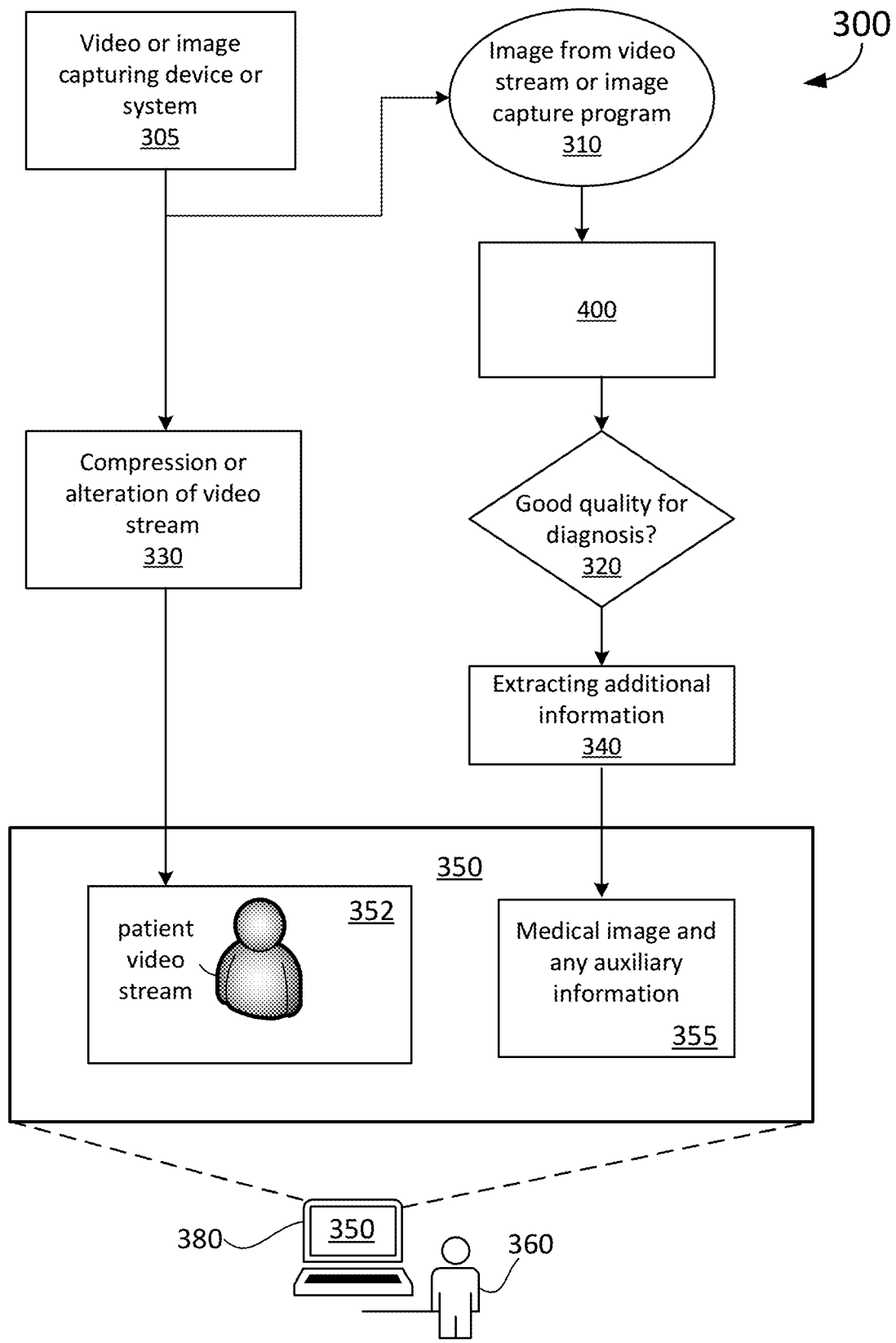
FIG. 3 shows a schematic diagram illustrating an example process of using one or more trained machine learning model to classify an image in a teleconference environment, in accordance with an example embodiment.

FIG. 3 shows a schematic diagram illustrating an example process 300 of using one or more trained machine learning model 170 to classify an image in a teleconference environment, in accordance with an example embodiment. A video conference (using video conference software application or facility) may be in process, facilitated by a video capturing system 305 (e.g. a web camera and associated software components), such as a raspberry Pi™ device. A patient (not shown) may use the video capturing system 305 to conduct the video conference in real time with a medical professional or a clinician 360. The clinician 360 may use a computer system 380 with the display device 350. The display device 350 may present two screens at once: a video conference screen 352 showing the patient and his or her environment, and a medical image screen 355 showing a relevant medical image 310 and any additional auxiliary information.

The medical image 310 may be taken as a raw image from a video stream (which has a plurality of images taken at consecutive timestamps) produced by the video capturing system 305. Alternatively, the medical image 310 may be uploaded by the patient using a customized software from a web portal.

The medical image 310 is uncompressed and sent to the system 400 for classification using one or more trained machine learning models 170, in accordance with an example process 200 described in FIG. 2. In some embodiments, the system 400 may be a remote system connected to the computer system 380 via a network (e.g. internet). In some embodiments, the system 400 may be a local system connected to the computer system 380 via a local network. In some embodiments, the system 400 may be the computer system 380.

The classification model 250 of the system 400 may generate a classification result at step 320, classifying the image 310 as good quality or bad quality. When the image 310 is classified as a good quality diagnostic photo, any additional, additional auxiliary information may be extracted at step 340 by the classification model 250 of the system 400 based on the trained machine learning models 170. For example, the additional auxiliary information regarding the image 310 may include one or more of: a dosage information, a likely diagnosis, or a treatment recommendation, such as "4 out of 5 dermatologist models suggested use a topical steroid of medium strength in this area." As the convolutional network can be trained on images or image segments that are important and possess good quality, the diagnostic sensitivity and specificity of the algorithm may be improved.

In some embodiments, the image 310, when received from a video stream produced by the video conference and classified as a good quality image or bad quality image, may be sent to the clinician 360 that is the same user that trained the machine learning model 170. For example, the image 310 may be sent to the same user account that has been recorded by the system 400 that was the user account (same single source) used to originally train that machine learning model 170. In such a scenario, the clinician 360 may very well agree with their own digital avatar (digital twin) as represented by the machine learning model 170, or can note any discrepancies in classification for personal learning or for re-training of the machine learning model 170.

At step 330, which may be performed in parallel with classifying the medical image 310, the video stream from the video capturing system 305 may be compressed or otherwise pre-processed (e.g., alternation of lighting), and sent to the computer system 380 used by the clinician 360, so that the clinician 360 may talk to the patient in real time, while looking at the medical image 310 and the respective additional auxiliary information.

Figure 4:
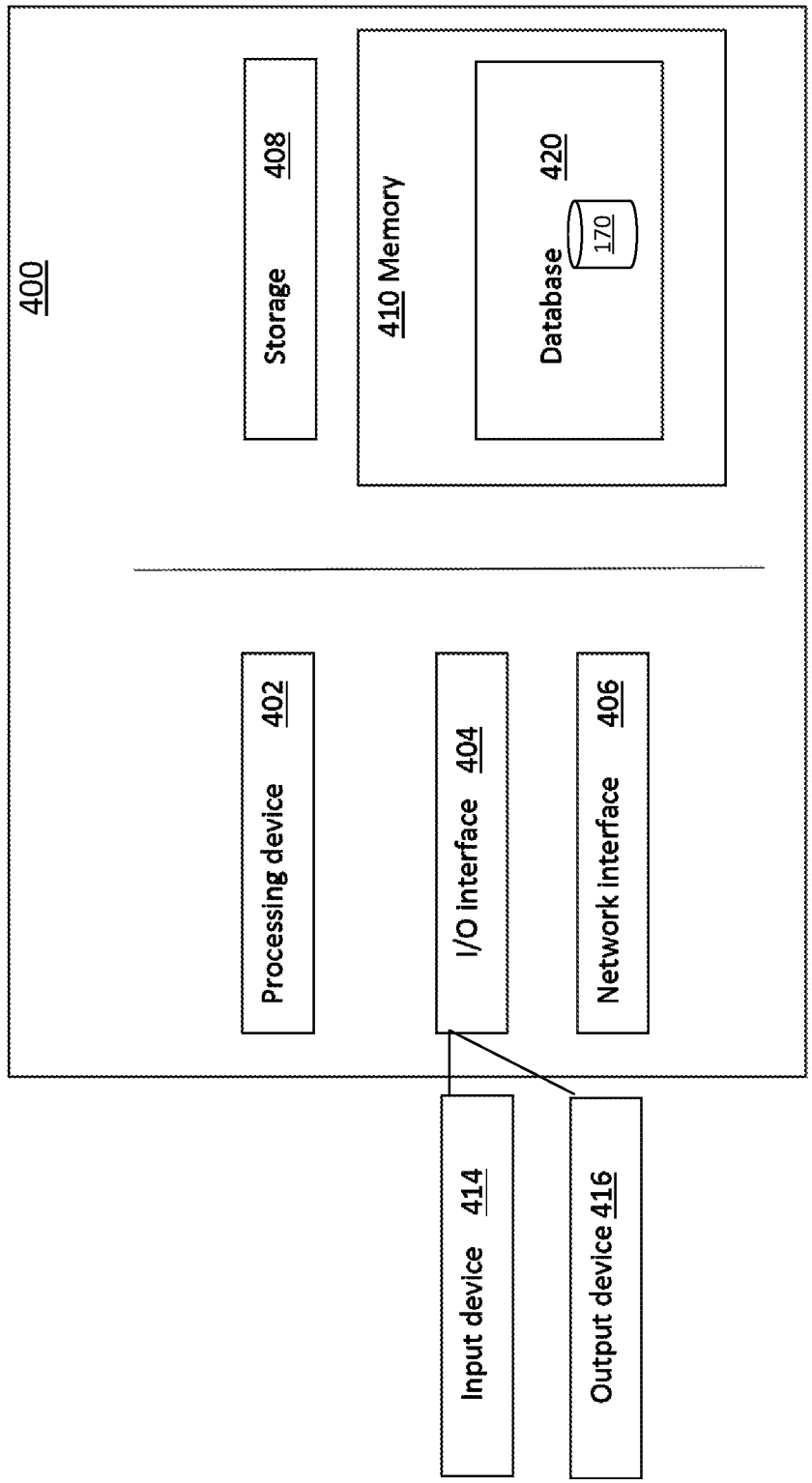
FIG. 4 illustrates an example schematic diagram showing a processing system for training and/or using an example machine learning model, in accordance with an example embodiment.

FIG. 4 illustrates an example schematic diagram showing the system 400 for training and/or using (e.g. inference) each example machine learning model 170, in accordance with an example embodiment. The system 400 can be implemented on one or more servers in one or more locations. In examples, the system 400 is a processing system in which example embodiments of the methods can be implemented.

One or more machine learning models 170 are stored in the memory 410 in a local database 420. The memory 410 in return interacts with the input/output (I/O) interface 404, which is connected to input device 414 and output device 416. The system 400 has a processing device 402 (e.g. a processor), the I/O interface 404, the network interface 406, persistent storage 408, and memory 410.

The processing device 402 may use instructions stored in the memory 410 to perform one or more methods as described herein.

Figure 11:
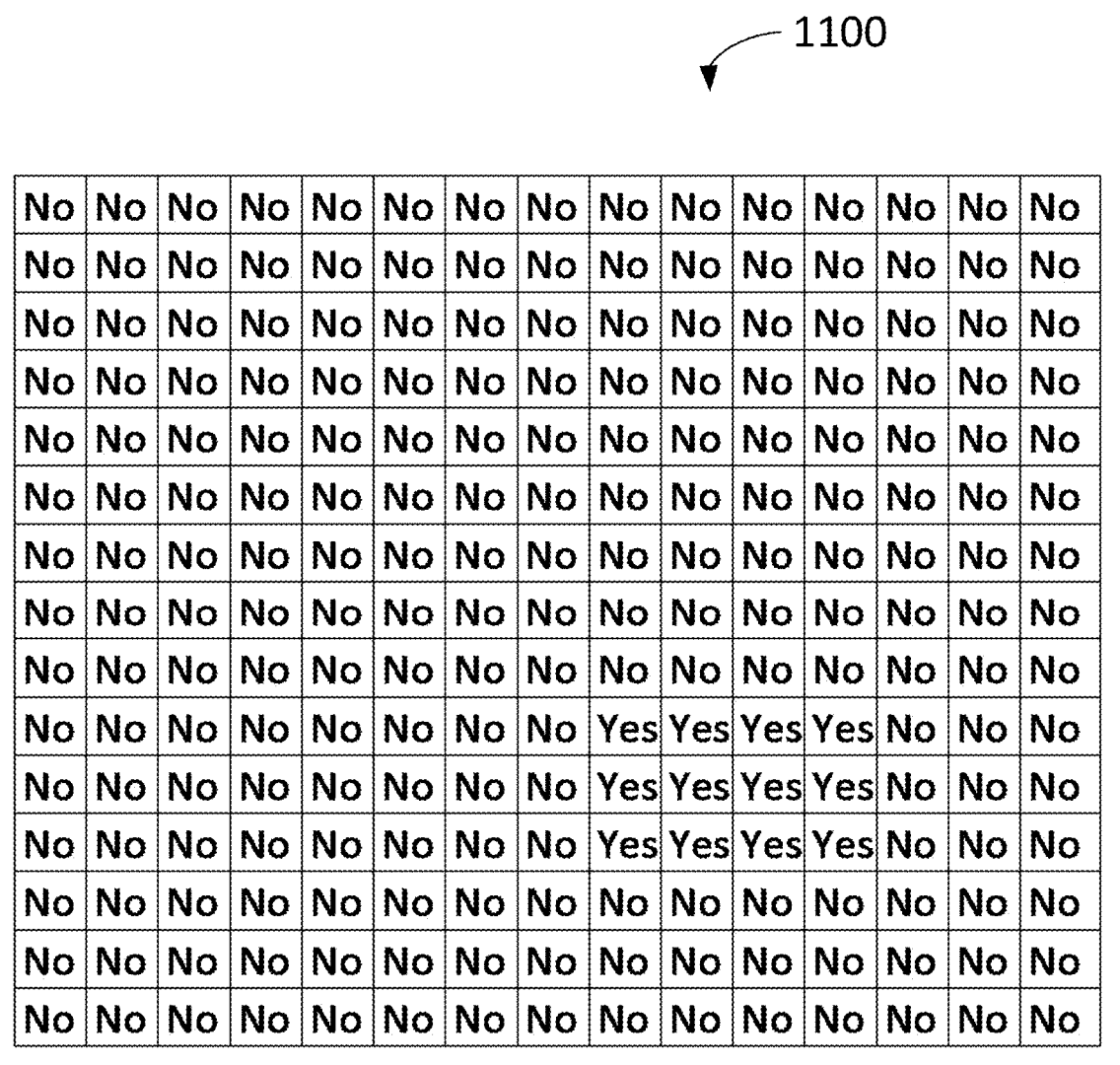

FIG. 11 shows an example of segmentation 1100 into pixel squares of a medical image 310, for the trained machine learning model 170 to classify the image 310 as suitable for medical or clinical diagnosis versus not. For example, each pixel square represents a medical image segment of the image 310. The example segmentation 1100 in FIG. 11 shows 15×15 pixel squares (225 in total), and it would be understood that there can be more or fewer pixel squares in other examples. As illustrated in FIG. 11, the trained machine learning model 170 can classify, for each pixel square, "yes" (positive label and good image, which can also be represented as "1" or other value) versus "no" (negative label and bad image, which can also be represented as "0" or other value). In the present example, twelve of the pixel squares are classified as "yes" and the remaining two hundred and thirteen pixel squares are classified as "no". In an example, when a threshold amount of the plurality of image segments are classified as the positive image segment by the trained machine learning model 170, then the trained machine learning model 170 classifies the entire image 310 as being a positive medical image for medical or clinical diagnosis. In an example, the threshold amount can be a particular number of pixel squares (e.g. ten). In an example, the threshold amount can be a particular ratio of "yes" versus "no". In various examples, the threshold is set by an operator or dynamically generated by the trained machine learning model 17. Similarly, when the amount of image segments classified as the positive image segment are below the threshold, the entire image 310 can be classified as being a negative medical image for medical or clinical diagnosis.

Reference is now made to FIGS. 5 to 10, which illustrate a number of example images that may be sent to the system 400 for the classification model 250 to use one or more of the trained machine learning models 170, as described above in connection with FIGS. 2 and 3.

Figure 5:
FIG. 5 shows an example image that is of sufficient quality to classify as an image that can be used for medical diagnosis.

FIG. 5 shows an example image 500 that is of sufficient quality to classify as an image that can be used for medical diagnosis. The image 500 has white lighting, is well lit and in focus, and its diagnostic features are apparent. This image 500 would be classified as a good quality or positive image by the classification model 250 having one or more trained machine learning models 170. In examples, with a positive classification, the system 400 can send the image 500 to the clinician 360 for medical or clinical diagnosis. In an example, the image 500 is transmitted to the computer system 380 of the clinician 360 using video conference software application. In an example, the image 500 is transmitted to the computer system 380 of the clinician 360 in an uncompressed state.

Figure 6:
FIG. 6 shows an example image that does not have sufficient quality to classify as an image that is not suitable for medical diagnosis.

FIG. 6 shows an example image 600 that does not have sufficient quality to classify as an image that can be used for medical diagnosis. The original image 600 is poorly lit, and has blurry, yellow-red lighting likely caused by incandescent bulbs. This image 600 would be classified as a bad quality or negative image by the classification model 250 having one or more trained machine learning models 170. In examples, with a negative classification, the system 400 does not send the image 500 to the computer system 380 of the clinician 360 for review and diagnosis, and therefore bandwidth is preserved. The system 400 may request that the patient take capture another image with their camera. In examples, the iterative or back-and-forth between the system 400 and the patient is automatically continued until an image is classified as being a good image. Therefore, the time of the clinician 360 is not wasted and bad quality images are not transmitted to the computer system 380 of the clinician 360. In some examples, if after several iterations it was not possible to obtain a good image, then an in-person consultation with the clinician 360 may be required.

Figure 7:
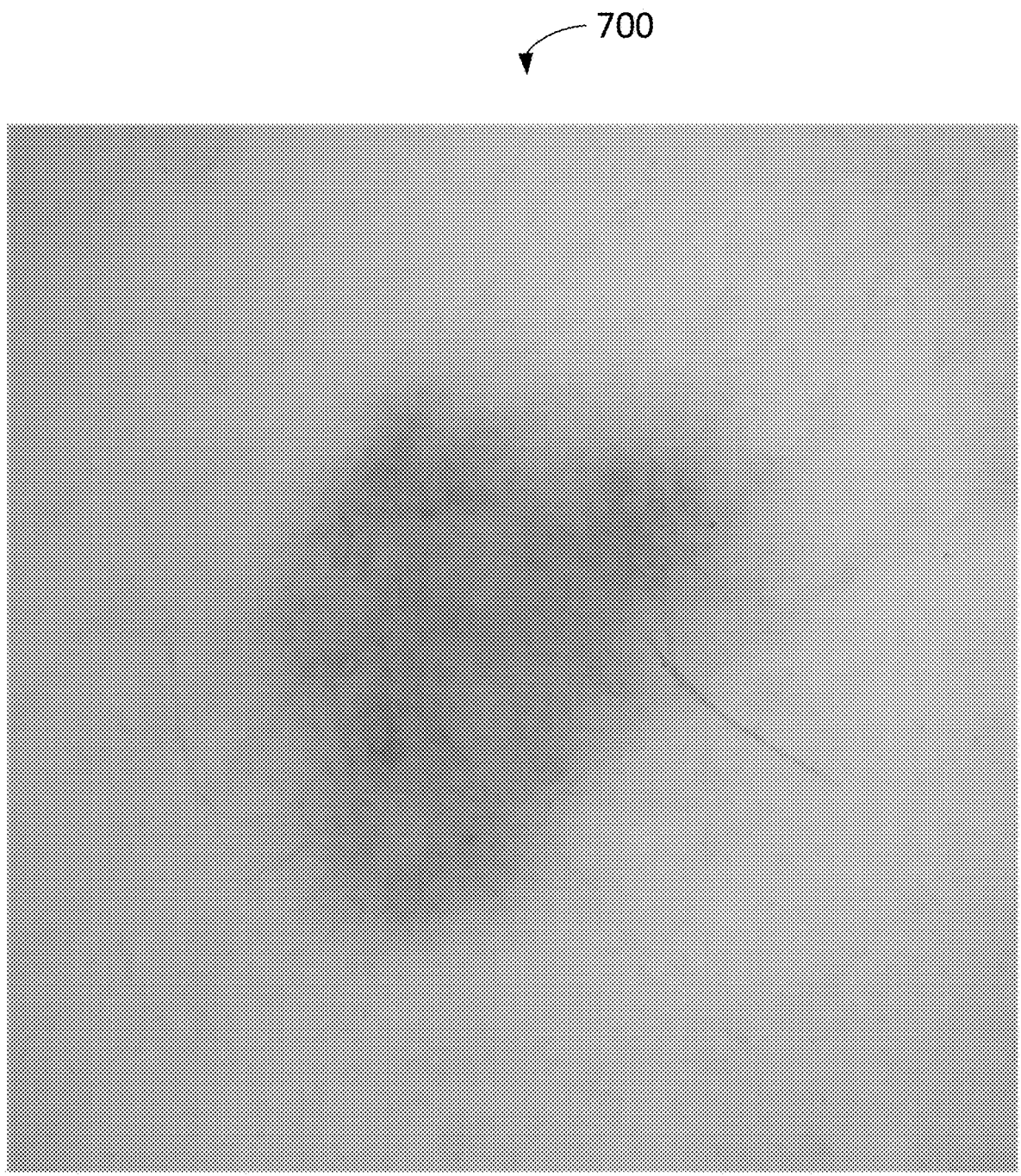
FIG. 7 shows another example image that is of sufficient quality to classify as an image that is suitable for medical diagnosis.

FIG. 7 shows an example dermatoscopic image 700 that is of sufficient quality to classify as an image that can be used for medical diagnosis. The dermatoscopic image 700 shows a lesion in focus. There is no obstruction. The reticulated pigment network is clearly visible. This dermatoscopic image 700 would be classified as a good quality or positive image by the classification model 250 having one or more trained machine learning models 170.

Figure 8:
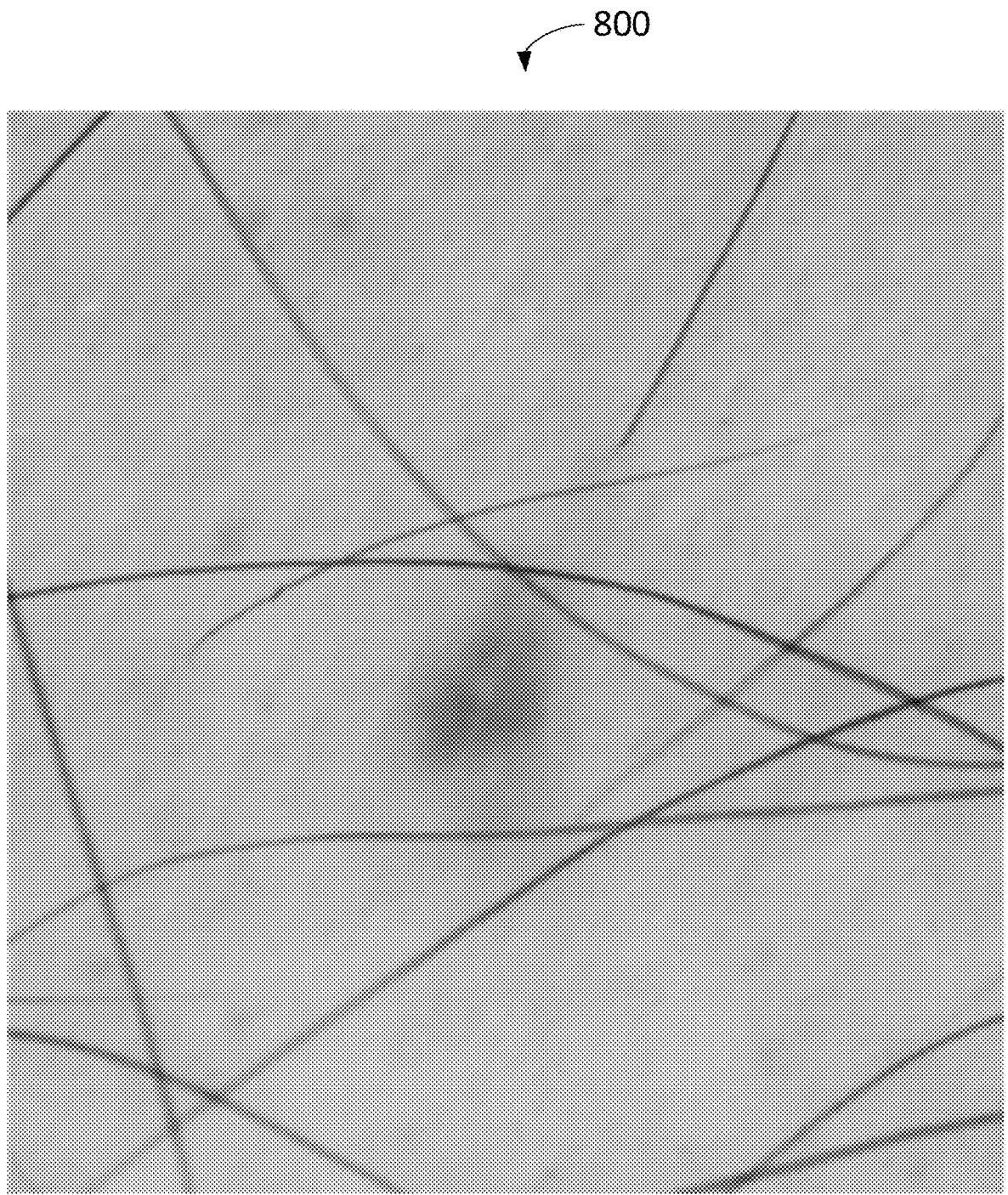
FIG. 8 shows another example image that does not have sufficient quality to classify as an image that is not suitable for medical diagnosis.

FIG. 8 shows an example dermatoscopic image 800 that does not have sufficient quality to classify as an image that can be used for medical diagnosis. The dermatoscopic image 800 is blurry. The pigment network is not visible. The lesion is partially obscured by hair. This dermatoscopic image 800 may be classified as a bad quality or negative image by the trained machine learning model 170.

Figure 9:
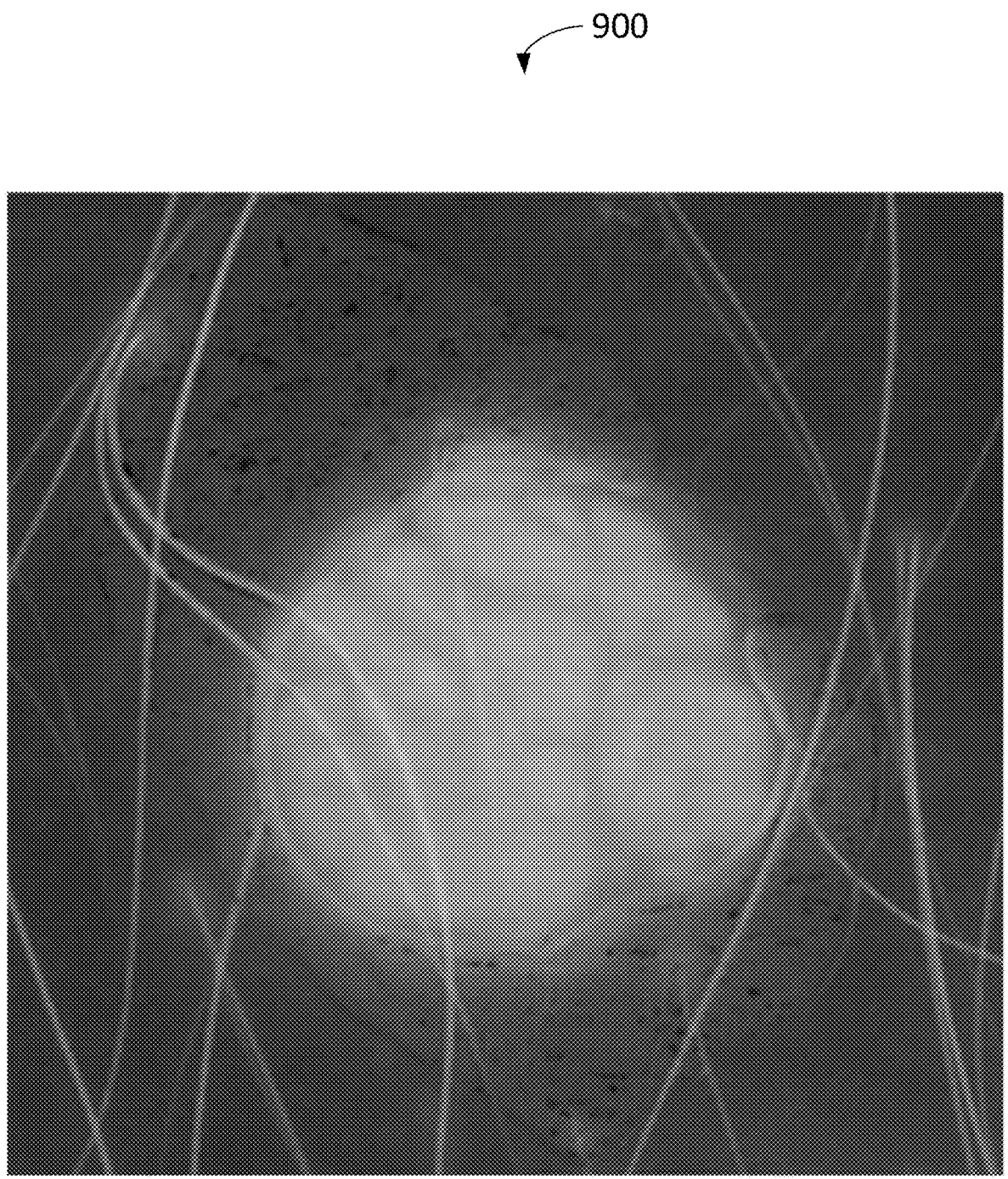
FIG. 9 shows another example image that is of sufficient quality to classify as an image that is suitable for medical diagnosis.

FIG. 9 shows an example spectrophotometric image 900 that is of sufficient quality to classify as an image that can be used for medical diagnosis. The spectrophotometric image 900 is targeted against vasculature using blood-specific wavelengths. The spectrophotometric image 900 is in focus. The vascular lacunae are clearly visible. There is no significant obstruction of the spectrophotometric image 900. This image 900 would be classified as a good quality or positive image by the classification model 250 having one or more trained machine learning models 170.

Figure 10:
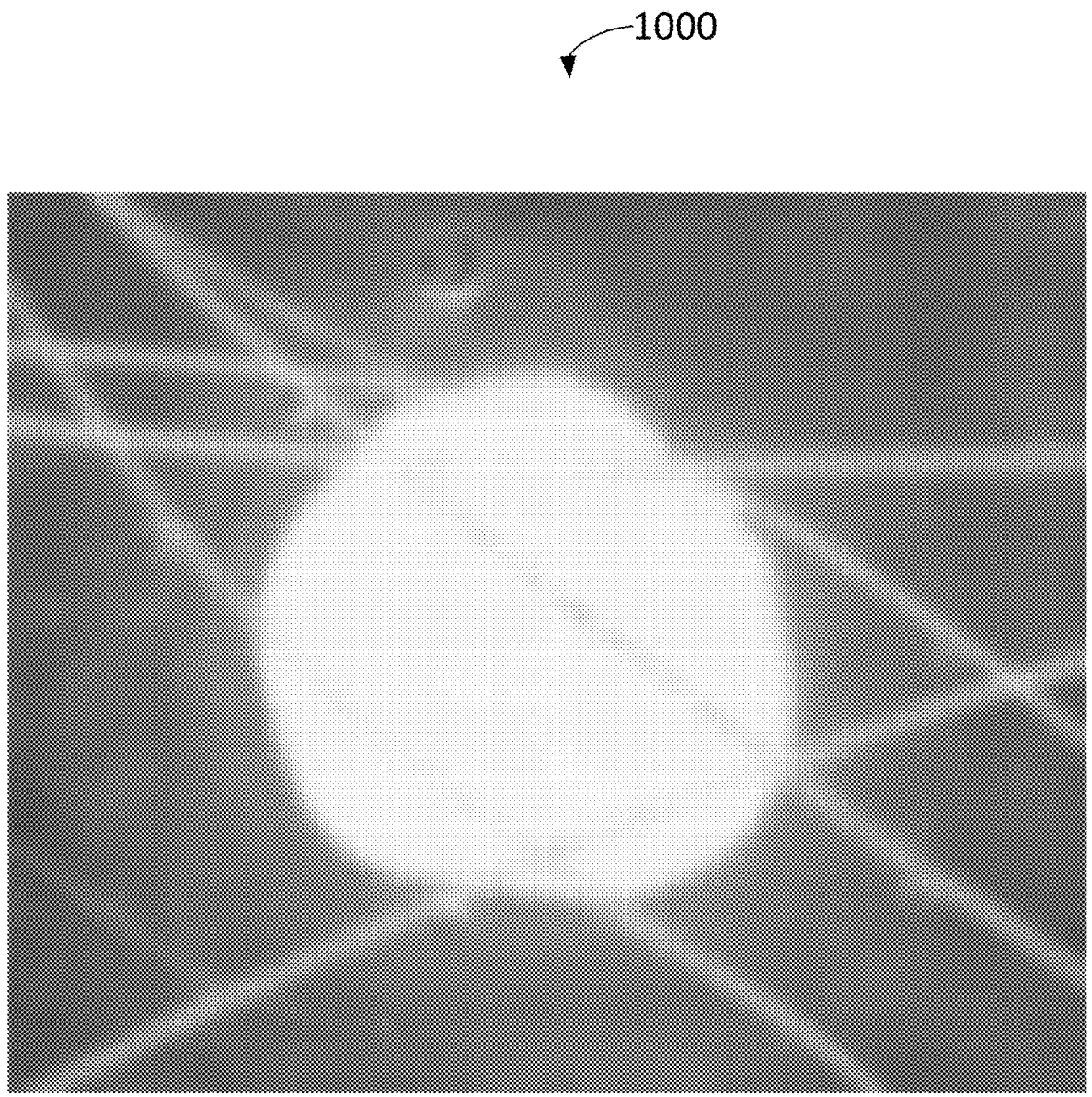
FIG. 10 shows another example image that does not have sufficient quality to classify as an image that is not suitable for medical diagnosis.

FIG. 10 shows an example spectrophotometric image 1000 that does not have sufficient quality to classify as an image that can be used for medical diagnosis. The spectrophotometric image 1000 is an example "bad quality" spectrophotometric image targeted against vasculature using blood-specific wavelengths. The spectrophotometric image 1000 is blurry. There is no clear definition of any underlying organized structures. There is significant obstruction and artifact with hair and fluid bubbles. This spectrophotometric image 1000 would be classified as a bad quality or negative image by the classification model 250 having one or more trained machine learning models 170.

In another example implementation for training of the trained machine learning model 170, the images in FIGS. 5 to 10 are each displayed to the clinician 360 on the display device 350, and the clinician 360 inputs the above-noted label classifications (positive versus negative) for training of the respective trained machine learning model 170 that represents the opinion of that clinician 360.

Example embodiments may be implemented as a system, a method, and/or a computer program product. The computer program product may include a computer-readable storage medium (or media) storing computer-readable program instructions that, when executed by a processor, cause the processor to carry out aspects of example embodiments. The computer-readable storage medium may be, for example, an electronic storage device, a magnetic storage device, an optical storage device, an electromagnetic storage device, a semiconductor storage device, or any suitable combination of these. A non-exhaustive list of more specific examples of the computer-readable storage medium includes: a portable computer disk, a hard disk, a random access memory (RAM), a read-only memory (ROM), a flash memory, an optical disk, a memory stick, a floppy disk, a mechanically or visually encoded medium (e.g., a punch card or bar code), and/or any combination of these. A computer-readable storage medium, as used herein, is to be construed as being a non-transitory computer-readable medium. It is not to be construed as being a transitory signal, such as radio waves or other freely propagating electromagnetic waves, electromagnetic waves propagating through a waveguide or other transmission media (e.g., light pulses passing through a fiber-optic cable), or electrical signals transmitted through a wire.

It will be understood that computer-readable program instructions can be downloaded to respective computing or processing devices from a computer-readable storage medium or to an external computer or external storage device via a network, for example, the Internet, a local area network, a wide area network and/or a wireless network. A network interface in each computing/processing device may receive computer-readable program instructions via the network and forwards the computer-readable program instructions for storage in a computer-readable storage medium within the respective computing or processing device. Computer-readable program instructions for carrying out operations of example embodiments may be assembler instructions, machine instructions, firmware instructions, configuration data for integrated circuitry, or either source code or object code written in any combination of one or more programming languages.

All statements herein reciting principles, aspects, and implementations of example embodiments, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of example embodiments. Similarly, it will be appreciated that any flowcharts, flow diagrams, state transition diagrams, pseudocode, and the like represent various processes which may be substantially represented in computer-readable program instructions. These computer-readable program instructions may be provided to a processor or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowcharts, flow diagrams, state transition diagrams, pseudo-code, and the like.

The computer-readable program instructions may also be loaded onto a computer, other programmable data processing apparatus or other devices to cause a series of operational steps to be performed on the computer, other programmable apparatus or other devices to produce a computer-implemented process, such that the instructions which execute on the computer, other programmable apparatus, or other device implement the functions/acts specified in the flowcharts, flow diagrams, state transition diagrams, pseudo-code, and the like.

In some alternative implementations, the functions noted in flowcharts, flow diagrams, state transition diagrams, pseudo-code, and the like may occur out of the order noted in the figures. For example, two blocks shown in succession in a flowchart may, in fact, be executed substantially concurrently, or the blocks may sometimes be executed in the reverse order, depending upon the functionality involved. It will also be noted that each of the functions noted in the figures, and combinations of such functions can be implemented by special-purpose hardware-based systems that perform the specified functions or acts or by combinations of special-purpose hardware and computer instructions.

It will be understood that, although the terms first, second, third, etc. may be used herein to describe various elements, these elements should not be limited by these terms. These terms are used to distinguish one element from another. Thus, a first element discussed below could be termed a second element without departing from the teachings of example embodiments. As used herein, the term "and/or" includes any and all combinations of one or more of the associated listed items.

It will be understood that when an element is referred to as being "connected" or "coupled" to another element, it can be directly connected or coupled to the other element, or intervening elements may be present (e.g., indirect connection or coupling). By contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.). Additionally, it will be understood that elements may be "coupled" or "connected" mechanically, electrically, communicatively, wirelessly, optically, and so on, depending on the type and nature of the elements that are being coupled or connected.

The terminology used herein is only intended to describe particular representative embodiments and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The functions of the various elements shown in the figures, including any functional block labeled as a "processor," may be provided through the use of dedicated hardware as well as hardware capable of executing instructions, in association with appropriate software instructions. When provided by a processor, the functions may be provided by a single dedicated processor, by a single shared processor, or by a plurality of individual processors, some of which may be shared. In some example implementations, the processor may be a general-purpose processor, such as a central processing unit (CPU) or a processor dedicated to a specific purpose, such as a digital signal processor (DSP). Moreover, explicit use of the term a "processor" should not be construed to refer exclusively to hardware capable of executing software, and may implicitly include, without limitation, an application-specific integrated circuit (ASIC), a field-programmable gate array (FPGA), a read-only memory (ROM) for storing software, a random access memory (RAM), and non-volatile storage. Other hardware, conventional and/or custom, may also be included.

Software modules, or simply modules or units which are implied to be software, may be represented herein as any combination of flowchart elements or other elements indicating the performance of process steps and/or textual description. Such modules may be executed by hardware that is expressly or implicitly shown. Moreover, it should be understood that a module may include, for example, but without limitation, computer program logic, computer program instructions, software, stack, firmware, hardware circuitry, or a combination thereof, which provides the required capabilities. It will further be understood that a "module" generally defines a logical grouping or organization of related software code or other elements as discussed above, associated with a defined function. Thus, one of ordinary skill in the relevant arts will understand that particular code or elements that are described as being part of a "module" may be placed in other modules in some implementations, depending on the logical organization of the software code or other elements, and that such modifications are within the scope of the disclosure as defined by the claims.

As used herein, the term "determine" generally means to make a direct or indirect calculation, computation, decision, finding, measurement, or detection. In some cases, such a determination may be approximate. Thus, determining a value indicates that the value or an approximation of the value is directly or indirectly calculated, computed, decided upon, found, measured, detected, etc.

It will be understood that, although the embodiments presented herein have been described with reference to specific features and structures, various modifications and combinations may be made without departing from such disclosures. The specification and drawings are, accordingly, to be regarded simply as an illustration of the discussed implementations or embodiments and their principles as defined by the appended claims, and are contemplated to cover any and all modifications, variations, combinations or equivalents that fall within the scope of example embodiments.

The invention claimed is:

1. A method for training a machine learning model, the method comprising:
receiving a dataset comprising a plurality of medical images;
receiving, from a first single source, a respective label for each one of the plurality of medical images, the respective label being a positive response versus a negative response, wherein the positive response as the respective label for the respective medical image is an indication that the medical image has a quality sufficient for medical diagnosis, without indicating the medical diagnosis on the medical image;

receiving a gaze profile for each one of the plurality of medical images from the first single source;

dividing each one of the plurality of medical images into a plurality of medical image segments;

associating each one of the plurality of medical image segments with an image segment label based on the respective label for the respective medical image being divided;

for each medical image of the plurality of medical image segments from the plurality of medical images, when the respective image segment label is a positive response: generating a gaze label based on the number of gaze hits for each one of the plurality of medical image segments for the medical image based on the received gaze profile for the medical image, and associating each one of the plurality of medical image segments with the respective gaze label; and sending a first set of labelled datasets to the machine learning model to train the machine learning model to identify image segments as having the quality sufficient for medical diagnosis for the first single source, wherein each labelled dataset in the first set includes a respective medical image segment of a medical image associated with a gaze label and an image segment label, the gaze label indicates that the number of gaze hit of the medical image segment being above a threshold, and the image segment label is the positive response.

2. The method as claimed in claim 1, wherein the gaze profile is generated based on tracking eye movements of the first single source and comprises a distribution of gaze hits from the first single source for the respective medical image.

3. The method as claimed in claim 2, wherein the respective label for each one of the plurality of medical images comprises a binary value.

4. The method as claimed in claim 3, wherein the binary value represents the positive response versus the negative response.

5. The method as claimed in claim 4, wherein the respective image segment label for each one of the plurality of medical image segments comprises an image segment binary value that represents the positive response versus the negative response, wherein the image segment binary value is based on the binary value of the respective label for the medical image containing the medical image segment.

6. The method as claimed in claim 1, wherein the machine learning model is not trained to make any medical diagnosis based on any of the plurality of medical images.

7. The method as claimed in claim 1, wherein each one of the plurality of medical image segments has a minimum dimension of 224 pixels by 224 pixels.

8. The method as claimed in claim 7, wherein each one of the plurality of medical image segments has a dimension of 256 pixels by 256 pixels.

9. The method of claimed in claim 1, further comprising, before receiving the respective label for each one of the plurality of medical images, re-sizing each one of the plurality of medical images to a minimum of 720 pixels on one side of the respective medical image.

10. The method as claimed in claim 9, wherein the re-sizing of each one of the plurality of medical images is to 1024 pixels on the one side of the respective medical image.

11. The method as claimed in claim 1, wherein the machine learning model comprises at least one of: a support vector machine (SVM), linear regression, or a convolutional neural network (CNN).

12. The method as claimed in claim 1, wherein the medical images include dermatological images.

13. The method as claimed in claim 1, further comprising:

receiving, from a second single source, a respective second label for each one of the plurality of medical images, the respective second label being the positive response versus the negative response;

associating each one of the plurality of medical image segments of each one of the plurality of medical images with a second image segment label based on the respective second label for the respective medical image being divided; and receiving a second gaze profile for each one of the plurality of medical images from the second single source;

generating a second gaze label based on the number of gaze hits for each one of the plurality of medical image segments for the medical image based on the received second gaze profile for the medical image; and sending a second set of labelled datasets to the machine learning model to train the machine learning model using the respective second gaze label for each of the plurality of medical images and the second image label for each of the plurality of medical image segments from the plurality of medical images.

14. The method as claimed in claim 1, further comprising:

receiving additional information regarding each one of the plurality of medical images from the first single source; and associating each one of the plurality of medical images with the respective additional information;

wherein the training of the machine learning model further comprises training the machine learning model for the first single source using: the respective additional information of each one of the plurality of medical images.

15. The method as claimed in claim 14, wherein the additional information regarding each one of the plurality of medical images comprises one or more of: a dosage information, or a treatment recommendation.

16. The method as claimed in claim 1, wherein at least one of the plurality of medical images is captured from a camera.

17. The method as claimed in claim 1, wherein the method is performed by a processing device.

18. The method as claimed in claim 1, the method further comprising: sending a second set of labelled datasets to the machine learning model to train the machine learning model, wherein each labelled dataset in the second set includes a respective medical image segment of a medical image associated with a gaze label and an image segment label, the gaze label indicates that the number of gaze hit of the medical image segment being less than a threshold, and the image segment label is the negative response.

19. A system for training a machine learning model, the system comprising:

a processing device; and a memory coupled to the processing device, the memory storing machine-executable instructions that, when executed by the processing device, cause the processing device to:

receive a dataset comprising a plurality of medical images;

receive, from a first single source, a respective label for each one of the plurality of medical images, the respective label being a positive response versus a negative response, wherein the positive response as the respective label for the respective medical image is an indication that the medical image has a quality sufficient for medical diagnosis, without indicating the medical diagnosis on the medical image;

receive a gaze profile for each one of the plurality of medical images from the first single source;

divide each one of the plurality of medical images into a plurality of medical image segments;

associate each one of the plurality of medical image segments with an image segment label based on the respective label for the respective medical image being divided; and send a first set of labelled datasets to the machine learning model to train the machine learning model to identify image segments as having the quality sufficient for medical diagnosis for the first single source, wherein each labelled dataset in first set includes a respective medical image segment of a medical image associated with a gaze label and an image segment label, the gaze label indicates that the number of gaze hit of the medical image segment being above a threshold, and the image segment label is the positive response.

20. A non-transitory computer readable medium containing program instructions for causing a processing device to perform a method of training a machine learning model, the instructions including:

instructions for receiving a dataset comprising a plurality of medical images;

instructions for receiving, from a first single source, a respective label for each one of the plurality of medical images, the respective label being a positive response versus a negative response, wherein the positive response as the respective label for the respective medical image is an indication that the medical image has a quality sufficient for medical diagnosis, without indicating the medical diagnosis on the medical image;

instructions for receiving a gaze profile for each one of the plurality of medical images from the first single source;

instructions for dividing each one of the plurality of medical images into a plurality of medical image segments;

instructions for associating each one of the plurality of medical image segments with an image segment label based on the respective label for the respective medical image being divided;

for each medical image of the plurality of medical image segments from the plurality of medical images, when the respective image segment label is a positive response: instructions for generating a gaze label based on the number of gaze hits for each one of the plurality of medical image segments for the medical image based on the received gaze profile for the medical image, and instructions for associating each one of the plurality of medical image segments with the respective gaze label; and instructions for sending a first set of labelled datasets to the machine learning model to train the machine learning model to identify image segments as having the quality sufficient for medical diagnosis for the first single source, wherein each labelled dataset in the first set includes a respective medical image segment of a medical image associated with a gaze label and an image segment label, the gaze label indicates that the number of gaze hit of the medical image segment being above a threshold, and the image segment label is the positive response.

* * * * *